United States Patent
Wenz et al.

(12)

(10) Patent No.: US 6,485,754 B1
(45) Date of Patent: Nov. 26, 2002

(54) BONE CEMENT PASTE CONTAINING AN ANTIBIOTIC

(75) Inventors: Robert Wenz, Wollstradt (DE); Berthold Nies, Frankisch-Crumbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/402,120

(22) PCT Filed: Mar. 17, 1998

(86) PCT No.: PCT/EP98/01546

§ 371 (c)(1),
(2), (4) Date: Jan. 18, 2000

(87) PCT Pub. No.: WO98/43685

PCT Pub. Date: Oct. 8, 1998

(30) Foreign Application Priority Data

Apr. 1, 1997 (DE) .......................................... 197 13 229

(51) Int. Cl.⁷ .......................... A61K 33/42; A61K 9/00; A61K 31/70; A61K 47/00
(52) U.S. Cl. ....................... 424/602; 424/405; 424/409; 424/422; 424/423; 424/426; 424/489; 424/601; 514/25; 514/27; 514/769; 514/772
(58) Field of Search .............................. 424/600, 602, 424/601, 484, 405, 409, 422, 423, 426, 489; 514/25, 769, 27, 772

(56) References Cited

U.S. PATENT DOCUMENTS

| | | | | |
|---|---|---|---|---|
| 4,291,013 A | * | 9/1981 | Wahlig et al. | 424/16 |
| 4,587,268 A | * | 5/1986 | Pfirrmann | 514/774 |
| 4,610,692 A | * | 9/1986 | Eitenmuller et al. | 424/422 |
| 4,772,468 A | | 9/1988 | Pfirrmann | 424/602 |
| 4,853,225 A | * | 8/1989 | Wahlig et al. | 424/423 |
| 4,869,906 A | | 9/1989 | Dingeldein et al. | 424/426 |

FOREIGN PATENT DOCUMENTS

| | | | |
|---|---|---|---|
| EP | 0 147 021 | | 7/1985 |
| EP | 0-147-021 | * | 7/1985 |
| EP | 0 242 672 | | 10/1987 |
| WO | WO-96/36562 A1 | * | 11/1996 |

* cited by examiner

*Primary Examiner*—Jose' G. Dees
*Assistant Examiner*—Frank Choi
(74) *Attorney, Agent, or Firm*—Millen, White, Zelano & Branigan, P.C.

(57) ABSTRACT

The invention relates to an injectable curable bone cement paste based on bioresorbable hydroxyapatite-like compounds comprising calcium phosphate, which contains a cationic antibiotic in the form of a salt, preferably of its sulfate, the curable biodegradable bone cement releasing the antibiotic in biologically active concentrations with depot-like action over a long period of time. The bone cements according to the invention are suitable for the treatment of infectious inflammations of the bone and of the bone marrow, in particular as a result of bone defects and bone fractures.

16 Claims, 1 Drawing Sheet

BONE CEMENT PASTE CONTAINING AN ANTIBIOTIC

This application is a 371 of PCT/EP98/01546, filed on Mar. 17, 1998.

The invention relates to an injectable curable bone cement paste based on bioresorbable hydroxyapatite-like compounds comprising calcium phosphate, which contains a cationic antibiotic in the form of a salt, preferably of its sulfate, the curable biodegradable bone cement releasing the antibiotic with depot-like action over a long period of time. The bone cements according to the invention are suitable for the treatment of infectious inflammations of the bone and of the bone marrow, in particular as a result of bone defects and bone fractures.

Naturally occurring bone mineral consists of calcium phosphate of hydroxyapatite structure. The composition of bone minerals here, however, does not correspond to the ideal stoichiometric composition of crystalline hydroxyapatite $(Ca_{10}(PO_4)_6(OH)_2)$, but as a rule has a non-stoichiometric composition which is caused by the incorporation of other anions such as carbonate or hydrogenphosphate instead of ortho-phosphate but also of other cations such as sodium, potassium or magnesium instead of calcium.

For some years, it has been possible to prepare synthetic bone substitute material based on hydroxyapatite-like calcium phosphate compounds, which on account of its qualitative and structural similarity approaches natural bone. Thus the known disadvantages which can arise due to the obtainment of natural autogenic or allogenic bone can be avoided.

The properties of these synthetic hydroxyapatites, in particular the physiological acceptance, the demanded bioresorbability and the ability to be replaced by newly generated natural bone tissue, or stimulation of the growth thereof, depend on the degree of crystallization, which is pronounced to a greater or lesser extent, the particle size and the porosity which can be achieved in the preparation. These materials furthermore have the advantage that they resist mechanical stresses virtually exactly as well as natural bone, which suggests their use in the case of relatively large bone defects or fractures.

Such materials are disclosed, for example, in EP 0416 761, U.S. Pat. Nos 4,880,610, 5,053,212, EP 0664 133, EP 0 543 765 or WO 96/36562. WO 96/36562 discloses a hydroxyapatite bone cement which, on account of its almost amorphous structure, has an excellent bioresorbability and, despite its porosity, a good mechanical stability. This material, called α-BSM, can be prepared in the form of curable pastes which can easily be introduced into the defective bone by means of a syringe.

In the case of injuries to the bone, in particular in the case of open breaks or comminuted fractures, as a rule there is a considerable risk of infection. In principle, this can be combatted by addition of antibiotics. A local, single and limited-dose administration in the surgical care of the bone fracture merely causes only a small part of the infectious bacteria which have established themselves in the bone tissue and are very poorly accessible as a result of inadequate circulation to be killed. As a result, severe and life-threatening inflammations of the bone marrow or of the bone tissue can therefore occur in some cases.

In order to avoid this, antibiotic-containing polymer beads (DE 23 20 373, DE 26 51 441), for example, are introduced into the wound or medullary cavity in the wound-toilet and first dressing of the defective bone. The antibiotic can diffuse out of this polymer material over a relatively long period of time and thus display its bacteriocidal action in an adequate concentration. The disadvantage of this method is that the polymer material suitable for the release of the antibiotic is mostly not biodegradable or inadequately biodegradable such that after the healing of the bone it has to be removed again by means of a fresh operation.

The incorporation of the antibiotic directly into the synthetic bone cement used failed until now on the fact that no possiblities were found to release the antibiotic from the cement in delayed form over an adequately long period of time in biologically active concentrations including a toxicologically still justifiable total dose. As a rule, in such cases a very rapid release of the entire amount of antibiotic takes place.

It has now surprisingly been found that bone cements based on bioresorbable hydroxyapatite-like compounds comprising calcium phosphate release certain antibiotics which are present as certain salts over a long period of time in adequately high biologically active concentrations continuously from the cured bone cement into the medullary cavity and the surrounding tissue in the manner of an active compound depot having controllable release.

The great advantage of such a system according to the invention is that a second specific surgical intervention to remove non-biodegradable polymer materials which until now were widely used as an active compound depot for applications of this type is superfluous. Inflammatory processes in the bone marrow or bone tissue can thus be treated very simply at the same time as the reconstruction of the bone or else even prevented. This is time-saving, inexpensive and saves the patient the bother of a further surgical intervention including in-patient treatment.

Appropriate bone cements which cure in vivo using cationic antibiotic salts are particularly suitable here. According to the invention, the cement materials which are disclosed in EP 0 543 765 or WO 96/36562 are particularly preferred, but in particular α-BSM from WO 96/36562.

By "amorphous" as that term is used here, it is meant a material with significant amorphous character. Significant amorphous character contemplates greater than 75% amorphous content and preferably greater than 90% amorphous content and is characterized by a broad, featureless X-ray diffraction pattern. It is recognized that a small degree of crystallinity may exist in the material, however, it is anticipated, in the case of the amorphous components of the invention, that such crystallinity will not be greater than the degree of crystallinity desired in the product poorly crystalline hydroxyapatitic calcium phosphate.

"Reactive" is used herein to refer to the reactivity of the amorphous calcium phosphate of the present invention and with other calcium phosphates. The reactivity is characterized by the ability of the amorphous calcium phosphate to harden at 37 degrees C. in less than five hours and substantially harden in about one to five hours in the presence of a calcium phosphate or crystallization promoter. Completeness of the reaction, the rate of the reaction, homogeneity of the resultant product and ability to react with otherwise inert compounds are characteristic of the reactive ACP (amorphous calcium phosphate) of the invention.

The invention thus relates to a plastic, injectable, curable bone cement paste based on bioresorbable hydroxyapatite-like compounds comprising calcium phosphate, which contain a cationic antibiotic salt. The invention likewise relates to an appropriate active compound depot for use for the treatment and prophylaxis of osteomyelitis and osteitis, in particular as a result of bone defects and bone fractures. The system according to the invention is especially suitable, in particular for larger fractures and comminuted fractures having open and therefore easily infectable wounds.

It has been found that, of the group consisting of the cationic antibiotics, especially the aminoglycosides or certain peptide antibiotics, have the desired advantageous release properties.

Suitable aminoglycosides are, for example: amikacin, butirosin, dideoxykanamycin, fortimycin, gentamycin, kanamycin, lividomycin, neomycin, netilmicin, ribostamycin, sagamycin, seldomycin and epimers thereof, sisomycin, sorbistin, spectinomycin and tobramycin. The aminoglycosides not only exhibit outstanding release properties in the sense according to the invention but as a rule additionally exhibit a wide concentration-dependent spectrum of action. A preferred aminoglycoside in the sense of the invention is gentamycin.

Especially polymyxin B is to be emphasised from the series of suitable peptide antibiotics. Capreomycin, a β-lactamase inhibitor, furthermore also shows the desired action according to the invention.

It has furthermore been found that in addition to the type of antibiotic its administration form also plays an important part. Thus only the corresponding salts show the desired depot actions and release characteristics. Suitable salts in principle are inorganic and organic salts. Preferred inorganic salts are the sulfates, phosphates, hydrogenphosphates and chlorides, while in the case of the organic salts, the citrates, acetates and lactates are preferred. Particularly advantageous results are achieved, however, using the corresponding sulfates. The antibiotic which is very particularly preferred is accordingly gentamycin sulfate.

The invention thus relates to an injectable curable bone cement paste, or a corresponding active compound depot, based on bioresorbable hydroxyapatite-like compounds comprising calcium phosphate, which contain a cationic antibiotic salt, the antibiotic salt being an aminoglycoside salt, preferably an aminoglycoside sulfate, preferably gentamycin sulfate.

According to the invention, the corresponding bone cement powder based on compounds comprising calcium phosphate is mixed with an aqueous solution of the antibiotic, if appropriate with addition of auxiliaries such as stabilizers, preservatives, binders and/or complexing agents. Depending on the amount of liquid, a paste which is viscous to a greater or lesser extent results, which can be placed, for example, in a syringe.

The invention thus relates to a process for the production of an injectable curable bone cement paste based on bioresorbable hydroxyapatite-like calcium phosphate, comprising a cationic antibiotic salt, characterized in that bone cement powder based on compounds comprising calcium phosphate is mixed with an aqueous solution of the antibiotic, if appropriate with the addition of auxiliaries such as stabilizers, preservatives, binders and/or complexing agents.

Alternatively, of course, antibiotic and cement powder can also be mixed with one another directly before the appropriate amount of liquid is added.

The invention furthermore relates to the use of an appropriate bone cement powder based on compounds comprising calcium phosphate together with a cationic antibiotic salt for the production of an injectable, curable, bioresorbable, hydroxyapatite-like bone cement paste with the ability to release the antibiotic in vivo in biologically active concentrations after curing and over a long period of time, for the treatment and prophylaxis of osteomyelitis and osteitis, in particular as a result of bone defects or fractures.

As a rule, 0.3–1.5 ml of liquid (including all compounds dissolved or suspended therein) are added per approximately 1 g of cement powder (if appropriate including the antibiotic) for the production of the paste, depending on the desired consistency and the curing time dependent thereon. The concentration of the antibiotic, based on the bone cement, is 10–100 mg/g, preferably 40–50 mg, depending on the required activity and the intended amount of cement. Total doses of 300 mg of antibiotic should not be markedly exceeded for toxicity reasons if possible.

The antibiotic is preferably dissolved in the liquid. In this case, additionally known stabilizers and/or preservatives such as, for example, sodium benzoate, edetic acid, EDTA may be employed in concentrations (0.1–3%) customary for this purpose. In the case where the paste produced is to be applied by means of a syringe, binders can also be added to the liquid. Thus it has been shown that polyethylene glycol (PEG) produces a very soft paste and counteracts possible demixing on emptying of the syringe. According to the invention, other auxiliaries which can have an effect on the release, such as, for example, dextran sulfate, can also be included.

Suitable liquids according to the invention which are mixed with the bone cement powder are all liquids based on water, for example phosphate buffer, saline solution, blood or serum. In cases in which the antibiotic salt has adequate solubility, polar physiologically acceptable organic solvents, such as the already-mentioned PEG, can also be used.

Before the application of the antibiotic-containing paste by the physician, according to the invention the individual components can be prepared in individual separate packs (pre-packaging). One pack here contains the solid components (bone cement powder, bone cement powder+ antibiotic). Various pack sizes can be produced and offered for sale according to the size of the bone defect to be treated and/or according to the required antibiotic concentration (in the case where cement powder and antibiotic are mixed in solid form). The second pack consists of the liquid in which, in the preferrred embodiment, the antibiotic and optionally the auxiliaries mentioned are dissolved. Here too, various pack sizes (different amounts of liquid, or different antibiotic concentrations) can be prepared which are suited to the varying required amounts of cement of the first component.

The invention thus relates to a kit of parts essentially comprising the following separately packed components: (i) a defined amount of bone cement powder based on compounds comprising calcium phosphate and (ii) an amount of liquid suited thereto comprising a cationic antibiotic salt in an active concentration, if appropriate in the presence of stabilizers, preservatives, binders and/or complexing agents, the amount of liquid being selected such that after combining the two components (i) and (ii) an easily injectable curable paste results.

The invention in particular relates to an appropriate kit of parts comprising the said components in the following units: 1 g of (i) and 0.7 ml of (ii) with a variably adjustable antibiotic content of 10–100 mg/ml.

The invention furthermore relates to a kit of parts essentially comprising the following separately packed components: (i) a defined amount of bone cement powder based on compounds comprising calcium phosphate, blended with a cationic antibiotic salt in a biologically active concentration between 5 and 80 mg/g of cement powder, if appropriate in the presence of a stabilizer, preservative, binder and/or complexing agent and (ii) an amount of liquid suited thereto, which is selected such that after combination of the two components (i) and (ii) an easily injectable curable paste results.

After curing, the bone cement pastes according to the invention release antibiotic continuously, depending on the starting amount (20–60 mg of cement powder) over a period of time of up to 10 days in an almost constant concentration of approximately 500–100 µg/ml (Table 1, FIG. 1). This is a multiple of the biologically active minimum concentration of most antibiotics.

If on the other hand, cationic antibiotic salts are not used, but, for example, cephalosporins, the release of the antibiotic takes place completely within a few hours (Table 1, FIG. 1). Since the released antibiotic is rapidly diluted further and broken down in the body as a rule, it is obvious that in the case of such release kinetics bacteria which are poorly accessible and only develop in the course of time are not affected. As can furthermore be seen from the figure and the table, the carrier also plays a crucial part. Thus the antibiotic according to the invention (e.g. gentamycin sulfate) is released just as rapidly if other material is used instead of the hydroxyapatite-like cement pastes according to the invention.

With the aid of the bone cement pastes according to the invention not only inflammations of the bone and of the bone marrow in the case of bone defects can be prevented, but even inflammations which have already broken out can be gradually checked after the surgical intervention has taken place.

EXAMPLE 1

Figure 1:
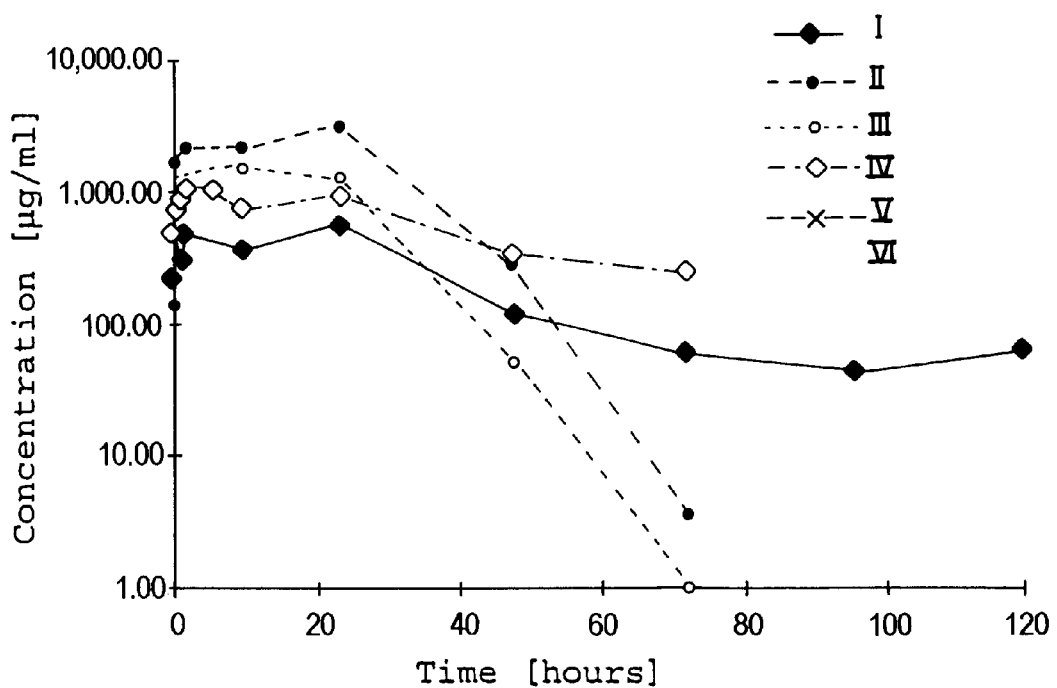
FIG. 1 shows the release of various antibiotics, gentamycin sulfate (=Refobacin ™) cefazolin (cephalosporin) and netilmycin sulfate, from -BSM cement after curing as a function of time. Corresponding kinetics with agar serve as a control. Table 1 shows the underlying individual values.

1 g of cement powder (α-BSM, WO 96/36562) and 0.7 ml of water in which 42 mg of gentamycin sulfate have been dissolved are mixed with one another. A paste is obtained by this means, which is shaped to give a ball of about 1 cm diameter. This ball is added at 37° C. to 20 ml of phosphate buffer according to Sörensen (pH 7.4). After approximately 10 minutes, the cement ball cures. At defined times, samples are taken from the buffer solution and the concentration of the antibiotic is determined microbiologically or chromatographically according to standard methods. The determined antibiotic concentrations in µg/ml correspond to the concentrations released in the buffer.

EXAMPLE 2

Analogously to Example 1, a previously cured ball of agar/gentamycin sulfate is eluted and the corresponding concentrations are measured.

EXAMPLE 3

Analogously to Example 1, an α-BSM/cefazolin ball is eluted and the corresponding concentrations are measured.

EXAMPLE 4

Analogously to Example 1, an α-BSM/netilmycin sulfate ball is eluted and the corresponding concentrations are measured.

TABLE 1

Elution of antibiotics from α-BSM µg/ml

| Hours | I | II | III | IV | V | VI |
|---|---|---|---|---|---|---|
| 0 | 245.96 | 139.64 | 478.57 | 484.78 | 0.00 | 0.00 |
| 0.5 | 474.46 | 1713.10 | 862.82 | 708.39 | 0.00 | 0.00 |
| 1 | 313.41 | 2036.00 | 1344.80 | 832.15 | 0.00 | 0.00 |
| 2 | 484.46 | 2199.20 | 1387.50 | 1021.00 | 0.00 | 0.00 |
| 6 | #NV | #NV | 1563.00 | 1009.40 | 0.00 | 0.00 |
| 10 | 364.25 | 2145.80 | 1554.80 | 751.94 | 0.00 | 0.00 |
| 24 | 565.89 | 3097.30 | 1189.10 | 906.52 | 0.00 | 0.00 |
| 48 | 116.19 | 273.63 | 50.16 | 332.69 | 0.00 | 0.00 |
| 72 | 58.00 | 3.46 | 1.00 | 243.59 | 0.00 | 0.00 |
| 96 | 42.77 | | | | 0.00 | 0.00 |
| 120 | 61.41 | | | | 0.00 | |

What is claimed is:

1. An injectable curable bone cement paste, based on bioresorbable compounds, said paste comprising reactive amorphous calcium phosphate, and a medicament, said medicament comprising a cationic antibiotic salt selected from gentamycin sulfate, tobramycin sulfate, amikacin sulfate and netilmycin sulfate.

2. A bone cement paste according to claim 1, wherein said paste consists essentially of bone cement powder comprising reactive amorphous calcium phosphate, a liquid and a medicament, said medicament comprising a cationic antibiotic salt selected from gentamycin sulfate, tobramycin sulfate, amikacin sulfate and netilmycin sulfate.

3. A bone cement paste according to claim 1, wherein said paste further contains polyethylene glycol.

4. A bone cement powder based on compounds comprising reactive amorphous calcium phosphate together with a cationic antibiotic salt for the production of an injectable, curable, bone cement paste with the ability to release the antibiotic in vivo in biologically active concentrations, after curing.

5. A process for the production of an injectable curable bone cement paste, based on bioresorbable reactive amorphous calcium phosphate, comprising a cationic antibiotic salt selected from gentamycin sulfate, tobramycin sulfate, amikacin sulfate and netilmycin sulfate, said process comprising:

mixing bone cement powder comprising reactive amorphous calcium phosphate with an aqueous solution of the antibiotic, optionally with the addition of stabilizers, preservatives, binders, complexing agents or combinations thereof.

6. A kit for the production of an injectable bone cement paste, said kit comprising the following separately packed components:
(i) a defined amount of bone cement powder based on compounds comprising reactive amorphous calcium phosphate and
(ii) an amount of liquid comprising a cationic antibiotic salt, in an active concentration, selected from gentamycin sulfate, tobramycin sulfate, amikacin sulfate and netilmycin sulfate, and optionally further comprising one or more stabilizers, preservatives, binders, complexing agents or combinations thereof,
wherein the amount of liquid is such that after combining the two components (i) and (ii) an easily injectable curable paste results.

7. A kit according to claim 6, wherein said kit contains 1 g of (i) per 0.7 ml of compound (ii) and component (ii) has an antibiotic salt content of 10–100 mg/ml.

8. A kit according to claim 6, wherein the cationic antibioitic salt has a biologically active concentration of from 40 to 50 mg per gram of bone cement powder.

9. A kit for the production of an injectable bone cement paste, said kit comprising the following separately packed components:
(i) a defined amount of bone cement powder based on compounds comprising reactive amorphous calcium phosphate, blended with a cationic antibiotic salt in a biologically active concentration of between 5 and 80 mg/g of bone cement powder, said cationic antibiotic salt selected from gentamycin sulfate, tobramycin sulfate, amikacin sulfate and netilmycin sulfate, and optionally further comprising one or more stabilizers, preservatives, binders, complexing agents or combinations thereof and
(ii) an amount of liquid such that after combination of the two components (i) and (ii) an easily injectable curable paste results.

10. In a method for the treatment and/or prophylaxis of osteomyelitis and osteitis comprising administering to a patient an active compound depot providing release of an antibiotic at biologically active concentrations, the improvement wherein said active compound depot comprises reactive amorphous calcium phosphate and a medicament, said medicament comprising a cationic antibiotic salt selected from gentamycin sulfate, tobramycin sulfate, amikacin sulfate and netilmycin sulfate.

11. A method according to claim 10, wherein said osteomyelitis and osteitis is a result of bone defects and/or fractures.

12. In a method for the treatment and/or prophylaxis of osteomyelitis and osteitis the improvement comprising administering to a patient an active compound depot providing release of an antibiotic at a concentration of from 100 to 500 $\mu$g/ml, wherein said active compound depot comprises reactive amorphous calcium phosphate and a medicament, said medicament comprising a cationic antibiotic salt selected from gentamycin sulfate, tobramycin sulfate, amikacin sulfate and netilmycin sulfate.

13. In a method for the reconstruction of bone comprising administering to a patient a bone cement material, the improvement comprising said bone cement material being a paste according to claim 1.

14. A bone cement paste comprising bone cement powder, a medicament, and liquid wherein said bone cement powder comprises reactive amorphous calcium phosphate, said medicament is a cationic antibiotic salt selected from gentamycin sulfate, tobramycin sulfate, amikacin sulfate and netilmycin sulfate, and said liquid is an aqueous medium or a physiologically acceptable polar organic solvent.

15. A bone cement paste according to claim 14, wherein said paste is formed by combining 0.3 to 1.5 ml of liquid per gram of bone cement powder.

16. A method of simultaneously providing bone reconstruction and treating inflammations of bone marrow or bone tissue, comprising administering to a patient a bone cement paste according to claim 1.

* * * * *